(12) United States Patent
Prestel et al.

(10) Patent No.: US 8,097,006 B2
(45) Date of Patent: Jan. 17, 2012

(54) SURGICAL SUTURE INSTRUMENT

(75) Inventors: Stephan Prestel, Rheinstetten-Morsch (DE); Florian Moser, Bretten (DE); Rolf Weber, Kraichtal (DE)

(73) Assignee: Richard Wolf GmbH, Knittlingen (DE)

( * ) Notice: Subject to any disclaimer, the term of this patent is extended or adjusted under 35 U.S.C. 154(b) by 610 days.

(21) Appl. No.: 12/240,338

(22) Filed: Sep. 29, 2008

(65) Prior Publication Data

US 2009/0088781 A1 Apr. 2, 2009

(30) Foreign Application Priority Data

Sep. 29, 2007 (EP) .................................... 07019216

(51) Int. Cl.
*A61B 17/04* (2006.01)
(52) U.S. Cl. ......................................................... 606/148
(58) Field of Classification Search .................. 606/139, 606/144, 148
See application file for complete search history.

(56) References Cited

U.S. PATENT DOCUMENTS

| | | | | |
|---|---|---|---|---|
| 4,957,498 A * | 9/1990 | Caspari et al. | ................. | 606/146 |
| 5,059,201 A * | 10/1991 | Asnis | ............................ | 606/144 |
| 5,387,221 A * | 2/1995 | Bisgaard | ....................... | 606/148 |
| 5,501,690 A * | 3/1996 | Measamer et al. | ............ | 606/146 |
| 5,591,179 A * | 1/1997 | Edelstein | ...................... | 606/144 |
| 5,797,927 A * | 8/1998 | Yoon | ............................. | 606/144 |
| 5,891,160 A * | 4/1999 | Williamson et al. | .......... | 606/144 |
| 5,897,564 A * | 4/1999 | Schulze et al. | ................. | 606/148 |
| 5,947,982 A * | 9/1999 | Duran | ............................ | 606/139 |
| 6,245,079 B1 * | 6/2001 | Nobles et al. | .................. | 606/144 |
| 6,723,107 B1 | 4/2004 | Skiba et al. | | |
| 6,896,686 B2 * | 5/2005 | Weber | ........................... | 606/145 |
| 7,112,208 B2 * | 9/2006 | Morris et al. | .................. | 606/144 |
| 7,572,265 B2 * | 8/2009 | Stone et al. | ..................... | 606/139 |
| 2002/0103493 A1 * | 8/2002 | Thal | ................................ | 606/144 |
| 2003/0065337 A1 * | 4/2003 | Topper et al. | ................. | 606/144 |
| 2003/0233106 A1 * | 12/2003 | Dreyfuss | ........................ | 606/144 |
| 2004/0199184 A1 * | 10/2004 | Topper et al. | ................. | 606/144 |
| 2004/0243135 A1 | 12/2004 | Koseki | | |
| 2004/0249394 A1 * | 12/2004 | Morris et al. | .................. | 606/144 |
| 2004/0260314 A1 * | 12/2004 | Lizardi et al. | ................. | 606/144 |
| 2005/0234479 A1 * | 10/2005 | Hatch et al. | .................... | 606/144 |
| 2005/0288690 A1 * | 12/2005 | Bourque et al. | .............. | 606/144 |
| 2007/0118150 A1 | 5/2007 | Weber | | |
| 2007/0123914 A1 * | 5/2007 | Lizardi et al. | ................. | 606/144 |
| 2007/0225735 A1 | 9/2007 | Stone et al. | | |
| 2007/0270885 A1 * | 11/2007 | Weinert et al. | ................ | 606/139 |

FOREIGN PATENT DOCUMENTS

DE 103 05 797 A1 8/2004
WO 2004/082725 A2 9/2004
* cited by examiner

*Primary Examiner* — Melanie Tyson
*Assistant Examiner* — Son Dang
(74) *Attorney, Agent, or Firm* — Panitch Schwarze Belisario & Nadel LLP

(57) ABSTRACT

A surgical suture instrument including a shank (2) on whose distal end a forceps jaw (4) is formed. The surgical suture instrument comprises a needle guide (30) through the forceps jaw (4). A receiver (40) for the releasable fastening of a needle holder (42) is formed on the shank (2), connected to the needle guide (30) on the proximal side of the needle guide (30).

10 Claims, 8 Drawing Sheets

SURGICAL SUTURE INSTRUMENT

CROSS-REFERENCE TO RELATED APPLICATIONS

This application claims priority to European Patent Application No. 07019216.6 filed Sep. 29, 2007. The contents of European Patent Application No. 07019216.6 are hereby incorporated by reference into the present application in their entirety.

BACKGROUND OF THE INVENTION

The invention relates to a surgical suture instrument. Suture instruments of the type being discussed here permit the tissue to be sutured. For example, ligaments can be gripped with a forceps jaw and subsequently pierced with a needle displaceably arranged in the suture instrument, wherein a thread with the needle is transported through the tissue.

Such suture instruments are known from US 2005/0288690 A1 as well as DE 103 05 797 A1. The suture instruments described there, in each case comprise a shank on whose distal end a forceps jaw with a stationary and a pivotable forceps jaw part is arranged. A curved guide channel which runs out at a side of the stationary forceps jaw part, which lies opposite the pivotable forceps jaw part, is formed on the stationary jaw part. The pivotable forceps jaw part includes an opening which corresponds to the position of the run-out of the guide channel, and through which the needle is led after the piercing of tissue held in the forceps jaw.

The suture instrument according to US 2005/0288690 A1 includes a needle, with which a lateral groove for receiving a thread is provided on a longitudinal side. A slot which is directed transversely to the longitudinal extension of the forceps jaw part and which creates an open connection to the guide channel, is provided corresponding to the position of the needle in the guide channel of the stationary forceps jaw part. The thread may be applied into the lateral groove of the needle via this slot. One disadvantage of this design is the fact that the thread, given an imprecise arrangement in the groove formed on the needle, may jam in the region of the guide channel, which connects to the groove on the distal side, and between the channel wall and the needle, so that the suture instrument is no longer capable of application. A further disadvantage with this instrument is the fact that the needle needs to be pushed via a feed channel extending in the shank over the complete shank length, to the guide channel of the stationary forceps jaw part. This is particularly difficult when curved needles which are adapted to the curvature of the guide channel are used.

With the suture instrument known from DE 103 05 797 A1, it is not necessary to transport the needle through the whole shaft to the guide channel of the stationary forceps jaw part. This suture instrument, on the proximal side of the stationary forceps jaw part, includes a longitudinal slot which communicates with the guide channel of the forceps jaw part. However, here too, the application of curved needles is problematic, since these can only be introduced into the longitudinal slot with some difficultly. A further disadvantage of this suture instrument is the fact that one may only apply needles to which a thread is fastened. This leads to the fact that a multitude of needle-thread combinations must be kept ready for differing suture tasks.

Basically, one may ascertain that the surgical suture instruments known until now are difficult to operate with regard to the insertion of the needle and/or have disadvantages with regard to operational reliability.

BRIEF SUMMARY OF THE INVENTION

Against this background, it is the object of the invention to provide a surgical suture instrument and such components for a surgical suture instrument which, with a simple construction, ensure an improved operational reliability and operating ability of the suture instrument.

This object is achieved by a surgical suture instrument, a needle holder, and a needle, with the features specified in the present disclosure. Advantageous further formations of the invention are to be deduced from present disclosure, including the specification, claims, and drawings.

The surgical instrument according to the invention comprises a shank on whose distal end a forceps jaw is formed. Moreover, the suture instrument has a needle guide through the forceps jaw. The basic idea of the invention lies in a receiver for the releasable fastening of a needle holder being formed on the shank, connecting to the needle guide at the proximal side.

For the releasable fastening of the needle holder, this receiver is designed in a manner such that a needle holder provided for receiving a needle may be quickly fastened to it or quickly released from it. The receiver may, for example, be formed as a recess on the shank on an outer side of the shank. At its distal end, the receiver typically has an open access to the needle guide.

Designed in such a manner, the invention permits the suture instrument to be equipped with a needle in a simple and quick manner. For this, a needle may be arranged spatially separated from the suture instrument in the needle holder, and the needle holder subsequently together with the needle may be fastened in or on the receiver formed in the shank. Since the needle holder, when it is located on the receiver formed on the shank, is arranged on the proximal side of the needle guide, preferably directly connected to the needle guide, when using suitable actuation means, the needle may be moved over a relatively short distance and in the most favorable case directly by the needle holder, into the needle guide of the suture instrument. Moreover, this design also renders it possible to provide the needle holder with a needle arranged therein in a premanufactured manner, which entails a significant time gain with the preparation of application of the suture instrument according to the invention. Then, an awkward insertion of quite a small needle into the instrument may be avoided. Instead of this, such a premanufactured needle holder with a needle is merely attached to the suture instrument. A further advantage of such pre-equipped needle holders is to be seen in the fact that the danger of injury to the user of the suture instrument according to the invention is eliminated when equipping the needle holder.

Advantageously, with the suture instrument according to the invention, a needle holder is provided, which comprises a needle guide for receiving and guiding a needle, and is releasably fastened on the receiver of the shank in a manner such that the needle guide in the needle holder connects to the needle guide through the forceps jaw.

Accordingly, the needle holder is designed and is arranged on the receiver of the shank, such that the needle guide formed on the needle holder represents a proximal extension of the needle guide through the forceps jaw. The needle holder preferably forms a part of the shank. For this, the receiver for the needle holder and which is provided on the shank may be formed by a recess on the shank, wherein the needle holder has a shape corresponding to the recess, so that the needle holder and the shank in the assembled condition form an aligned outer surface. A particularly slim constructional shape of the suture instrument according to the invention may be realized by way of this.

Usefully, fastening means for the releasable fastening of the needle holder on the receiver on the shank are provided on the shank and/or on the needle holder. These fastening means are preferably arranged such that they fix the needle holder in the region of its distal, as well as in the region of its proximal end, at least in one direction which points from the shaft radially to the needle holder. Here, the manner in which these fastening means fix the needle holder on the receiver provided on the shank, may basically be infinite. Thus, fastening means may be provided on the shank side or needle holder side, which, e.g., are designed for forming a plug connection or locking connection between the receiver and needle holder, or the fastening means may also be designed in a magnetically acting manner.

Preferably, the fastening means are designed in the manner of a bayonet closure. This permits a particularly simple and quick fastening and release of the needle holder to or from the receiver formed on the shank. For this, fastening means which may be stuck together to one another, are provided on the shank and here preferably on the receiver as well as the needle holder, wherein with a subsequent relative rotational movement of the needle holder with respect to the shank, they form a positive fit which secures the needle holder in the radial direction with respect to the longitudinal axis of the shank, but preferably however also in the axial and, as the case may be, tangential direction.

For forming such a bayonet closure type fastening of the needle holder on the receiver of the shank, advantageously a projection is formed on the shank, preferably on the receiver of the shank, and this projection is aligned transversely, preferably radially to a longitudinal axis of the shank. Here, the end region of the projection is widened in at least one direction transversely to the longitudinal extension of the projection.

Accordingly, the free end of the projection projects radially outwards from the projection in at least one direction. This design, with a corresponding design of a fastening means on the needle holder side, permits these fastening means to be applied onto the projection and to subsequently rotate or pivot the needle holder relative to the shank, in a manner such that the widening of the projection engages behind a region of the fastening means on the needle holder side, by which means the needle holder is fixed in the attachment direction of the fastening means on the needle holder side, transversely to the longitudinal axis of the shank, with a positive fit.

One further advantageous design of the suture instrument according to the invention envisages a thread guide being formed on a jaw part of the forceps jaw, wherein the thread guide crosses the needle guide through the forceps jaw. Here, the thread guide runs between the two jaw parts of the forceps jaw and preferably directly above an opening of the needle guide which is provided on a jaw part. The thread guide is usefully designed in a manner such that a thread may be applied over this opening of the needle guide in the manner of a loop. If with the application of the suture instrument, a needle is moved through the needle guide of the forceps jaw, the distal end of the needle engages the thread and together with the thread lying on at the tip, penetrates through the tissue which is held in the forceps jaw.

In order to be able to move the needle from the needle holder through the forceps jaw via the needle guide, the suture instrument according to the invention usefully comprises an actuation rod, which in the region of the receiver for the needle holder comprises engagement means for the engagement with a needle inserted in the needle holder.

This actuation rod is preferably movably guided in the shank parallel to its longitudinal axis and may be actuated with a handle arranged in the region of the proximal end of the shank. Preferably, an engagement means, preferably in the form of a projection which is aligned essentially transversely to the longitudinal extension of the actuation rod, or of a recess aligned transversely to the longitudinal extension of the actuation rod, is formed preferably in the region of the distal end on the actuation rod. With this design, a needle inserted in the needle holder usefully comprises a recess corresponding with a projection designed on the actuation rod side or, with a recess formed on the actuation rod side, a corresponding projection. By way of the actuation rod, the needle may be moved distally in the needle guide and preferably also afterwards proximally again by way of this positive-fit engagement.

The invention also relates to a needle holder which comprises a needle guide for receiving and guiding a needle. Furthermore, the needle holder is designed for the releasable fastening on a receiver of a shank of a surgical suture instrument. In particular, the needle holder according to the invention is designed for use with a surgical instrument according to the previous description.

For this reason, advantageously, fastening means are provided on the needle holder for its releasable fastening on the receiver on the shank of a surgical suture instrument. This type of fastening means is basically freely selectable, as long as these fastening means are complementary to fastening means which, as the case may be, are formed on the shank of the surgical suture instrument. The needle holder may be designed for multiple use or, as is preferably envisaged, is determined for disposable use, and may for example be designed as a plastic injection molded part. Preferably, the needle holder is arranged in the suture instrument according to the invention.

The needle guide in the needle holder is preferably a groove, which extends in the longitudinal direction and which ends at a distal end of the needle holder. With this, the groove may extend over the whole length of the needle holder. Advantageously, the groove however only extends over a part region of the needle holder, so that the proximal end of the groove is closed and in this manner forms an abutment for a needle to be arranged in the needle holder. This design permits a needle to be reproducibly arranged in the needle holder in a predetermined position defined by the abutment of the proximal needle end on the groove end. Accordingly, this design of the needle holder also ensures needles always being arranged in a fixed position in a suture instrument after the attachment of the needle holder on this suture instrument, in which position, for example, engagement means formed on the needles may come into engagement with engagement means of an actuation means provided in the suture instrument, for moving the needle.

In order to prevent a falling-out of the needle from the needle holder as much as possible, advantageously, means are provided, which cover the open side of the groove at least in sections. Accordingly, at least one component may be provided, which is arranged on the needle holder in a manner such that it extends above the groove and preferably essentially transversely to the groove. With regard to this component, it may be the case, e.g., of a web which extends transversely relative to the groove. In this manner, a needle located in the groove is secured against falling out of the groove in all directions transversely to the longitudinal extension of the groove.

Preferably, an elongate hole which is preferably aligned obliquely to the longitudinal extension of the needle holder is formed in the region of the proximal end of the needle holder. This elongate hole preferably runs from an inner side of the needle holder which in the installed condition bears on a receiver for the needle holder, formed on the suture instrument, to an outer side of the needle holder, which lies radially at the outside on the suture instrument in this condition. The elongate hole permits the accommodation of a fastening means which is arranged on the receiver for the needle holder on the suture instrument and which, as already described above, comprises a projection aligned normally to the contact surface of the receiver, wherein the projection at its free end has a widening in at least one direction transversely to its longitudinal extension. The needle holder is attached onto such a fastening means on the receiver side in a manner such that the widening of the fastening means on the receiver side is located above the elongate hole. With a subsequent rotation of the needle holder relative to the shank of the suture instrument, the widening provided on the receiver-side fastening means, may engage over a region of the needle holder located laterally on the longitudinal edge of the elongate hole, by which means the needle holder is fixed on the receiver of the suture instrument with a positive fit. In order to prevent the widening of the receiver-side fastening means projecting on the outside of the needle holder, the needle holder on this outer side may usefully comprise a recess, in which the widening of the receiver-side fastening means comes to bear, without thereby projecting beyond the outer side of the needle holder.

The invention further relates to a needle which in particular is provided for the application in a needle holder as well as a suture instrument according to the preceding description. This needle is formed by a preferably straight metal strip, which comprises a distal and a proximal end. A cutting edge is formed at the distal end of this material strip and extends essentially normally to the movement direction of the needle, or proceeding from an end-edge extending normally to the movement direction. According to the invention, a recess extending proximally and transversely to the end-edge or cutting edge and which has an edge on the proximal side, is designed in a non-cutting manner and is formed on the end-edge or cutting edge.

This design of the needle according to the invention advantageously permits a thread to be transported through the tissue to be sutured, wherein the thread lies on the distal end of the needle in a loop-like manner. With this, the thread is to be positioned relative to the needle such that it comes to bear on the edge of the distal end of the needle, which is designed in a non-cutting manner. In contrast to previously known needles of this type, there is no danger of the thread being damaged by the blade of the needle or being split open by this blade, and thus is moved back again on moving the needle back again out of the previously pierced tissue.

The recess formed on the end-edge or cutting edge is usefully designed only so wide, that it may ensure a secure insertion of a thread into this recess. The shape of the recess is basically infinite as long as it has an adequately large receiver edge for the thread, which is formed in a non-cutting manner and which is aligned transversely to the movement direction of the needle. The position of the recess on the end-edge or cutting edge in principle is also freely selectable, as long as it is ensured that the thread may be gripped by this recess. Thus this recess may be arranged on an edge region of this cutting edge, and form a non-cutting shoulder of the cutting edge, wherein the thread only comes into contact with this non-cutting shoulder.

Preferably, a groove is formed on the end-edge or cutting edge, which divides the cutting edge into two cutting edge sections distanced to one another, wherein the groove base is designed in a non-cutting manner. Accordingly, with this design, the groove which is arranged preferably essentially centrally in the cutting edge, forms the recess designed in a non-cutting manner. This design has the advantage that the thread is secured against a movement transverse to the movement direction of the needle, and thus may not slip laterally from the distal end of the needle.

In one advantageous design, the groove is designed in a manner such that the groove width tapers in the proximal direction. Thus the groove may for example be designed in a wedge-shaped manner, wherein the side edges of the groove, proceeding from the end-edge or cutting edge at which these side-edges are distanced the furthest from one another, taper obliquely to one another in the proximal direction of the needle. In order to simplify the penetration of tissue, the side edges of the groove may be designed in a cutting manner in their distal end region, wherein the proximal-side base region of the groove, which serves for receiving the thread, is however designed in a non-cutting manner.

In a preferred design, the width of the groove formed on the end-edge or cutting edge tapers in the proximal direction in a two-stage manner. With this, the two side walls of the groove in a first distal section of the groove form cutting edges, wherein a proximal section of the groove has a non-cutting edge and forms a receiver for a thread. Particularly advantageously, the groove extends over the whole width of the distal needle end. Proceeding from the two longitudinal sides of the needle, with this, the side edges of the groove may firstly taper to one another at a relatively obtuse angle, and taper to one another in a more acute manner in a section of the groove which connects thereto at the proximal side. The distal-side edges which taper to one another at an obtuse angle thereby are designed in a cutting manner and form the actual cutting edges. In this manner, the needle with this design comprises two cutting edges aligned obliquely to the movement direction of the needle, which in each case form a tip. With this embodiment, the groove thus extends over the complete width of the end-edge of the needle and the cutting edges themselves are designed running obliquely to this end-edge. However, it is also conceivable to design the distal end of the needle such that parts of the cutting edge run in the direction of the end-edge and, for example, the groove is designed in a narrower manner, so that it does not extend over the whole width of the end-edge, at the distal end.

In order to be able to move the needle according to the invention into a working position as well as an initial position by way of an actuation rod, the needle usefully comprises means which may come into engagement with an actuation rod of a surgical instrument. Here, it may be the case of recesses and projections which are formed on the needle and which serve for forming a positive fit with corresponding means provided on the actuation rod, as are described further above. Preferably, the needle at its longitudinal side and in the region of its proximal end comprises a recess running transversely to its longitudinal extension, into which recess a projection on an actuation rod and which is aligned transversely to the movement direction of this rod may engage. The needle according to the invention is preferably arranged in a needle guide of the needle holder according to the invention.

BRIEF DESCRIPTION OF THE SEVERAL
VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figures 1, 2, 3:
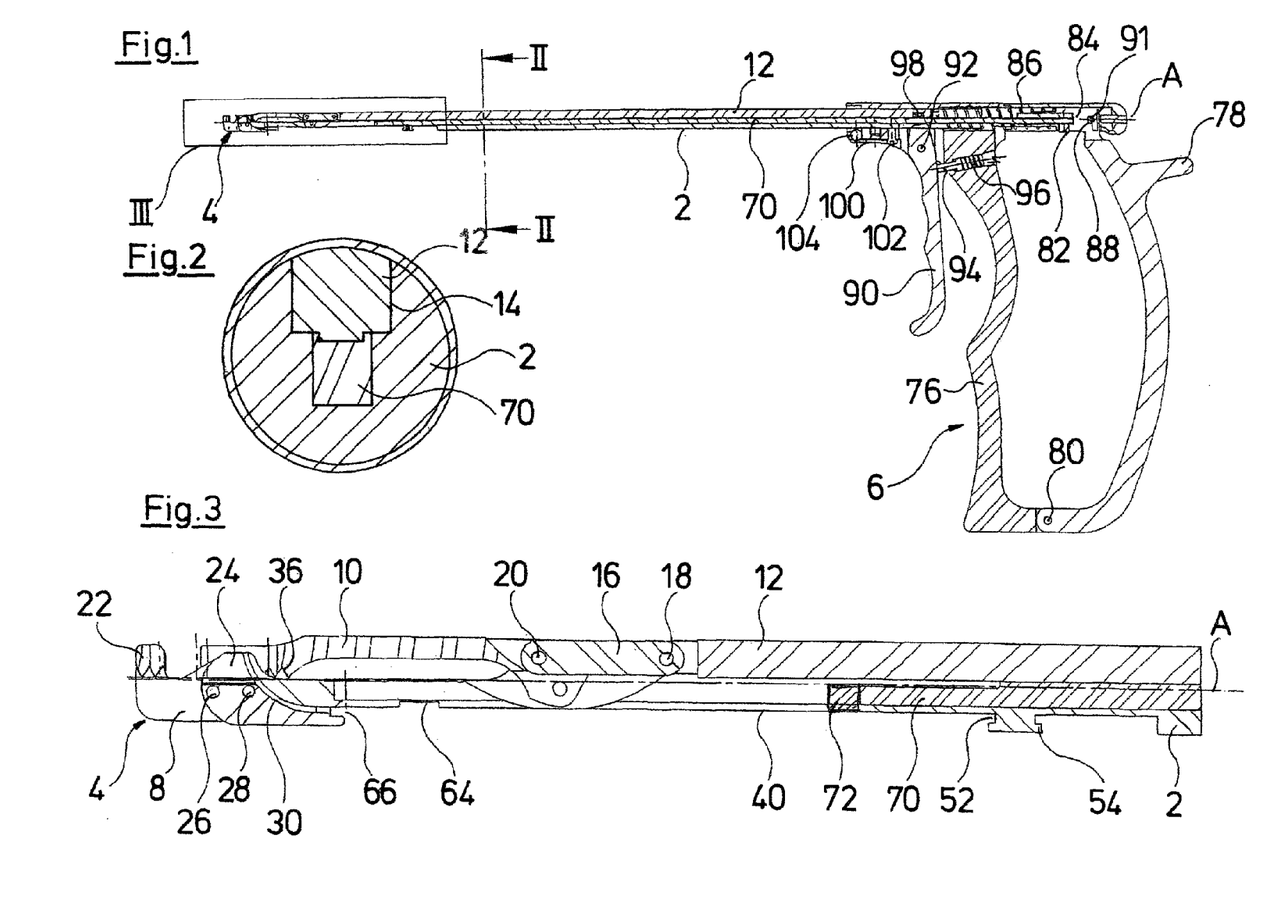
FIG. 1 is schematic longitudinal view of an embodiment of a surgical suture instrument.
FIG. 2 is a schematic cross-sectional view taken along line II-II in FIG. 1.
FIG. 3 is a schematic detail view of portion III of FIG. 1.

The surgical suture instrument represented in FIG. 1 comprises a shank 2, on whose distal end a forceps jaw 4 for firmly holding body tissue 110 (see FIG. 12) is formed. A handle 6 for holding and operating the suture instrument is arranged at the proximal end of the shank 2. The forceps jaw 4 comprises a first stationary jaw part 8 arranged on the shank 2, and a second jaw part 10 which is articulated on the shank 2 in a pivotable manner with respect to the jaw part 8.

The actuation of the forceps jaw 4 is effected via an actuation rod 12, which is displaceably guided in a groove 14 formed on the shank 2, parallel to a longitudinal axis A of the shank 2. For this, the jaw part 10 is coupled in movement to the actuation rod 12 via a joint part 16, wherein the joint part 16 is articulated on the distal end of the actuation rod 12 via a pin 18 and on the proximal end of the jaw part 10 via a pin 20.

The jaw part 8, as may be deduced from FIGS. 11 to 14, comprises a holding region 22 on the distal side, which is designed in a toothed manner. A slot 23, proceeding from the distal end of this holding region 22, extends proximally in the longitudinal direction of the shank 2. A needle guide component 24 which is fastened on the jaw part 8 via two pins 26 and 28, is arranged in this slot 23 on the proximal side of the holding region 22. The needle guide component forms a bump-like raised part which extends in a direction towards the second jaw part 10. A curved guide channel 30 is formed in the needle guide component 24 and this channel is part of a needle guide for a needle 32 and is led through the forceps jaw 4. This guide channel 30 extends to a side of the raised part of the needle guide component 24, namely, the side facing the second jaw part 10.

A groove 33 running in the longitudinal extension of the shank 2 and crossing a run-out 35 of the guide channel 30 which is arranged on the upper side of the raised part of the needle guide component 24, is formed on the outer side of the raised part of the needle guide component 24, the outer side facing the second jaw part 10. This groove 33 serves for guiding a thread 37 above the guide channel 30.

The jaw part 10 comprises an opening 34 for receiving the bump-like raised part of the needle guide component 24 as well as for leading through the needle 32. This opening 34 is arranged in the region of a holding region 36 which is designed in a toothed manner at the distal end of the jaw part 10. The opening 34 is also accessible from a longitudinal side of the jaw part 10 via a slot 38.

Figures 6, 6A:
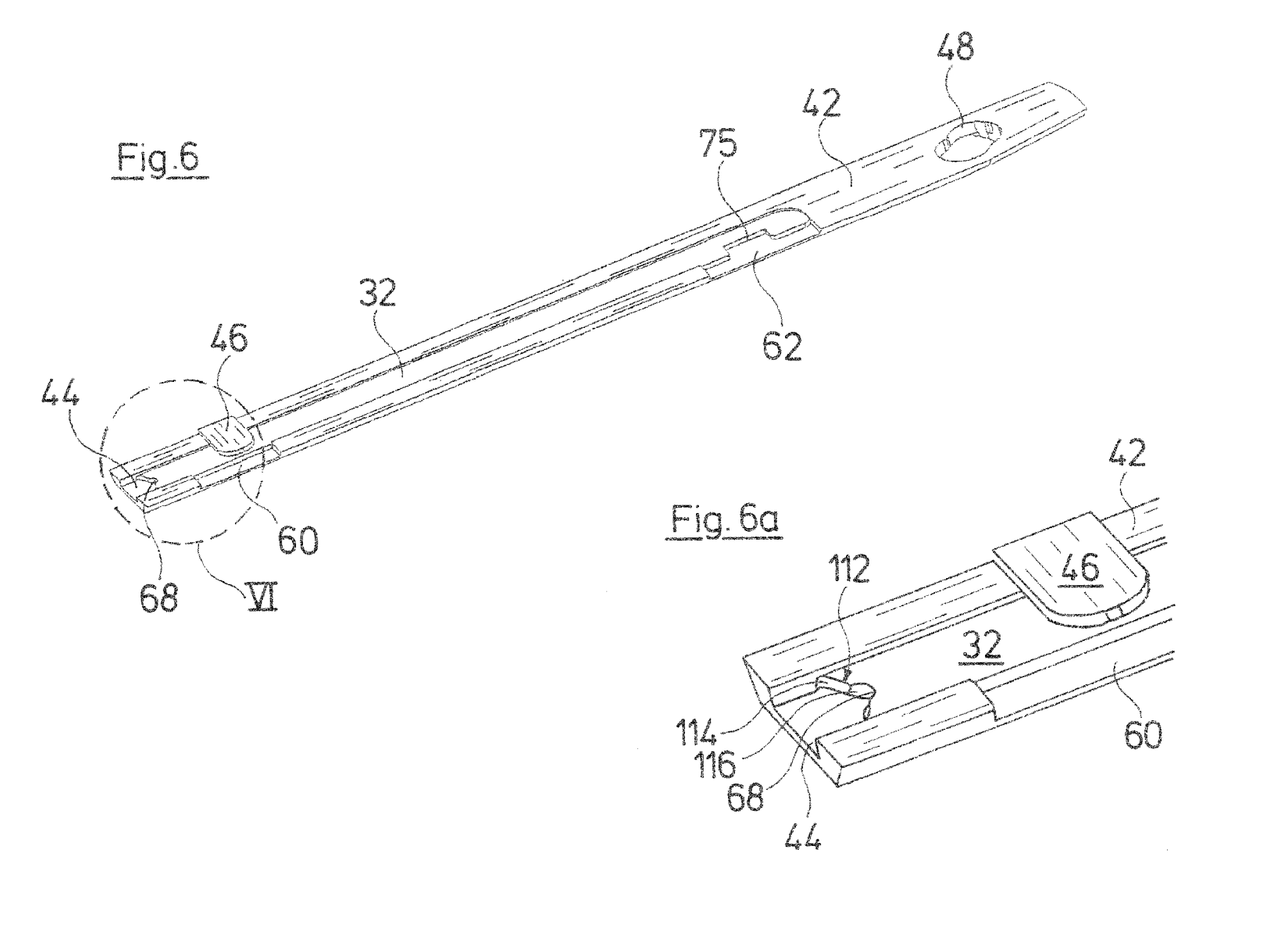
FIG. 6 is a schematic perspective longitudinal view of a needle holder with a needle arranged therein.
FIG. 6a is a schematic perspective detail view of portion VI of FIG. 6.

On the proximal side of the jaw part 8, the shank 2 of the surgical suture instrument comprises an elongate flattening or recess 40. This recess 40 forms a receiver for the needle holder 42 which is represented in FIG. 6 and which is intended for disposable use. The needle holder 42 has a shape corresponding to the recess 40 formed on the shank 2, so that its outer side is flush with the outer side of the shank 2 in the condition attached to the shank 2. A groove 44 which forms a needle guide for receiving and guiding a needle 32, is formed on the needle holder 42, proceeding from its distal end, on an inner side which faces the shank 2 in the attached condition. If the needle holder 42 is attached onto the needle guide component 24 on the proximal side, this groove 44 in the installed condition of the needle holder 42 is aligned with the guide channel 30 formed on the needle guide component 24, so that a needle 32 may be displaced from the groove 44 directly into the guide channel 30 of the needle guide component 24 and from there through the forceps jaw 4. The proximal end of the groove 44 is closed and forms an abutment for the needle 32. The dimensions of the groove 44 are adapted to the dimensions of the needle 32. Thus the width of the groove corresponds essentially to the width of the needle 32, wherein the length of the groove 44 is dimensioned such that the needle 32 may be accommodated completely in the groove 44. A component in the form of a web 46 is arranged above the groove 44 in the region of the distal end of the needle holder 42, and this component, proceeding from the wall of the needle holder 42 which delimits the groove 44, extends transversely to the longitudinal direction of the groove 44 essentially completely past this groove 44.

The needle 32 arranged in the needle holder 42 is formed by a straight metal strip. The distal end of the needle 32 forms a cutting edge 112. A groove 68 which divides the cutting edge 112 into two cutting edge sections distanced to one another, is formed on this cutting edge 112. The width of the groove 68, proceeding from the cutting edge 112, tapers in the proximal direction in a two-stage manner. With this, the two side edges of the groove 68, in a first distal region 114, firstly taper to one another in a relatively blunt manner. The side edges of the groove 68 taper to one another in a more acute manner in a second proximal region 116 of the groove 68 which connects to the first distal region of the groove 68. In a first distal region 114 of the groove 68, the side edges of this groove form the cutting edges. In a second proximal region 116 of the groove 68, its side edges and the groove base are designed in a non-cutting manner. This second proximal region 116 of the groove 32 serves for receiving a thread 37.

For fastening the needle holder 42 in the recess 40 formed on the shank 2 of the surgical suture instrument, the needle holder 42 in the region of its proximal end, comprises an elongate hole 48 which is aligned obliquely to the longitudinal extension of the needle holder 42. The axis of the elongate hole 48 runs normally to the bearing surface of the needle holder 42 on the shank 2. A circular recess 50 whose diameter corresponds to the length of the elongate hole 48, is formed around the elongate hole 48 at the outer side of the needle holder 42, which is distant to the groove 44. A projection 52 which extends radially outwards with respect to the longitudinal axis A of the shank 2 and which corresponds to the elongate hole 48 with recess 50, formed on the needle holder 42, is arranged on the shank 2 of the surgical suture instrument in the region of the recess 40. At its end, the projection 52 has a widening or prominence 54 which extends outwards in the longitudinal direction A of the shank 2 in opposite directions. The widening 54 has a shape and size which is complementary to the elongate hole 48.

Figure 7:
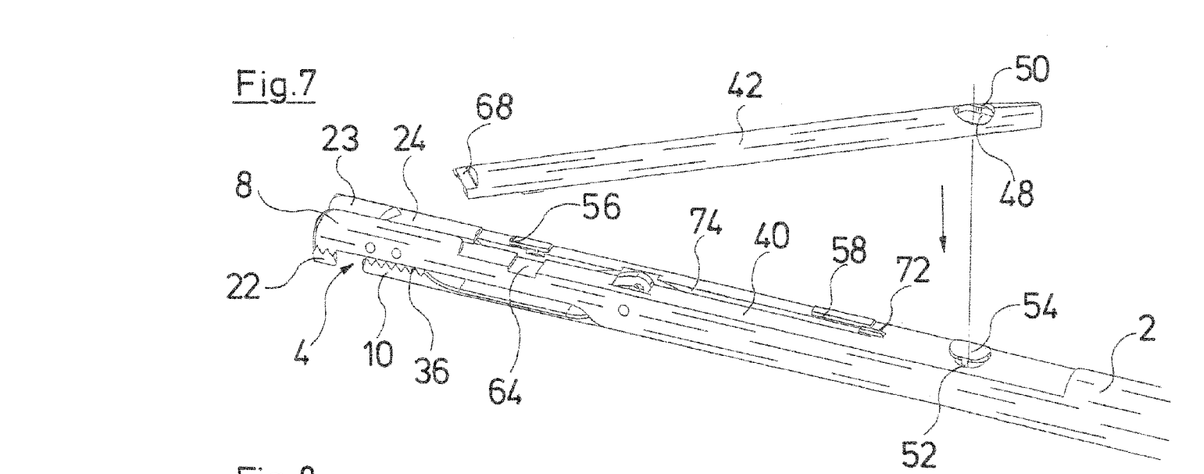
FIG. 7 is a schematic perspective exploded view of a distal end region of the instrument of FIG. 1 and the needle holder of FIG. 6.
Figure 8:
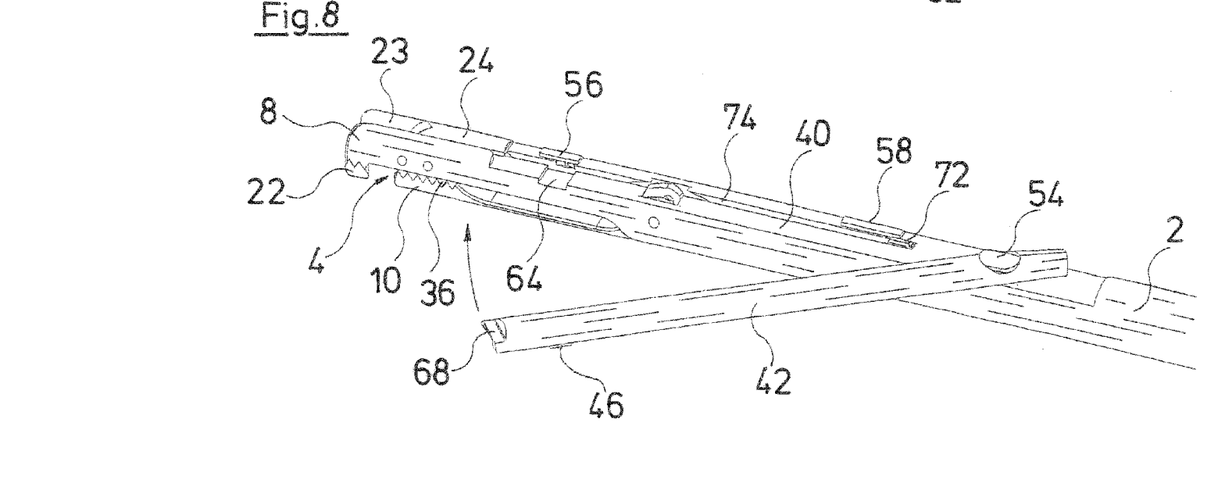
FIG. 8 is a schematic perspective longitudinal view of a distal end region of the instrument of FIG. 1 with the needle holder of FIG. 6 attached thereon.

The fastening of the needle holder 42 in the recess 40 is particularly evident from FIGS. 7 and 8. Firstly, the needle holder 42 is applied onto the recess 40, such that the projection 52 with the widening 54 formed thereon, engages into the elongate hole 48. On account of the arrangement of the elongate hole 48 which is aligned obliquely to the longitudinal direction of the needle holder 42, the needle holder 42 hereby is to be applied onto the recess 40 obliquely to the longitudinal axis A of the shank 2. Subsequently, the needle holder 42 is to be pivoted in the direction of the shank 2 until it is aligned with the shank 2, so that the longitudinal axis of the needle holder 42 is aligned parallel to the longitudinal axis A of the shank 2. In this position, the widening 54 of the projection 52 engages behind the needle holder 42 in the region of the recess 50 formed on the elongate holder 48, and thus fixes the needle holder 42 in the direction of the longitudinal extension of the projection 52, i.e. in the radial direction to the elongate axis A of the shank 2, in the manner of a bayonet closure. The proximal end of the needle guide component 24 extends past the recess 40 of the shank 2 for fixing the needle holder 42 at its proximal end, wherein it forms a slot 66. A shoulder 68 which corresponds to this slot 66, is formed at the distal end of the needle holder 42 on its outer side, and in the pivot position of the needle holder 42, which is aligned to the shaft 2, engages into the slot 66 and engages over the needle guide component with a positive fit.

For limiting the pivot path of the needle holder 42 relative to the shank 2, two projections 56 and 58 are formed in the region of the recess 40, which may be brought into engagement with two recesses 60 and 62 on the needle holder 42 adjacent to the groove 44. A recess 64 is machined in the recess 40 for receiving the component 46 covering the groove 44 of the needle holder 42.

An actuation rod 70 is provided for actuation of the needle 32 arranged in the needle holder 42. This actuation rod 70 is guided in movement in the groove 14 of the shank 2 directly next to the actuation rod 12. A slot nut 72 which is arranged at the distal end of the actuation rod 70, extends in a direction transverse to the longitudinal extension of the actuation rod 70 beyond the activation rod 70, and thus forms a projection. The slot nut 72 is guided in a longitudinal slot 74 formed on the recess 40, wherein the projection formed by the slot nut 72 projects into the recess 40. The movement coupling between the actuation rod 70 and the needle 32 is effected by way of the slot nut 72 being brought into engagement with a recess 75 which is arranged in the region of the proximal end of the needle 32 on a longitudinal edge. By way of this, a forwards and backwards movement of the needle 32 is possible by way of a corresponding displacement of the actuation rod 70.

Figure 15:
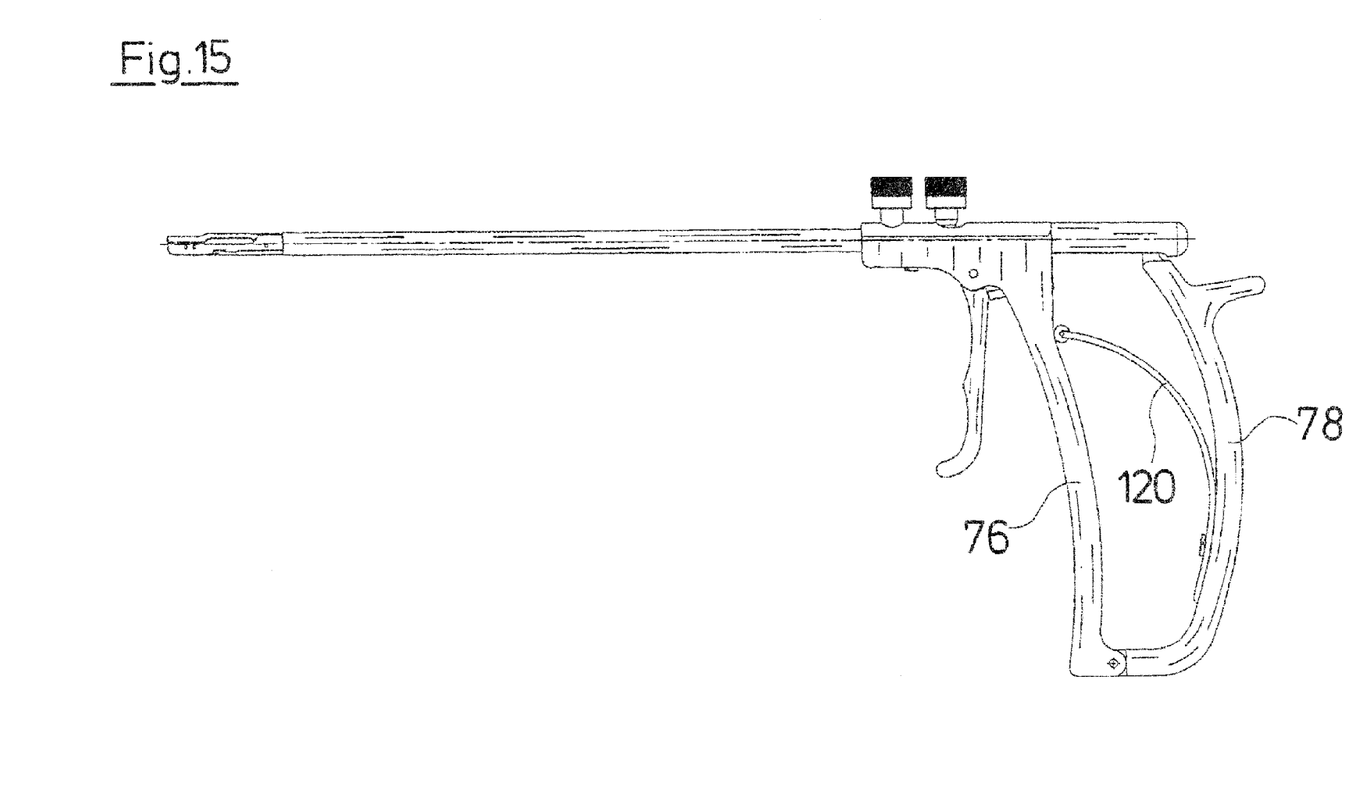
FIG. 15 is a schematic longitudinal view of another embodiment of a surgical suture instrument.

The handle 6 arranged at the proximal end of the shank 2 comprises a two-part grip, which is formed by a stationary, first grip part 76, on whose end distanced to the shank 2 a pivotable grip part 78 is articulated via a pin 80. The grip part 78 is arranged on the proximal side of the grip part 76. A slider 84 is fastened on the proximal end of the actuation rod 70 by way of a screw 82. The slider 84 is arranged in a region of the handle 6, in which this forms a proximal extension of the shank 2. In this region, the slider 84 is supported on a helical spring 86 arranged on the distal side of the slider 84, wherein in an alternative design represented in FIG. 15, one envisages the slider 84 being supported via the grip part 78 on a leaf spring 120 arranged between the grip parts 78 and 76. A slot 88 running transversely to the longitudinal axis A of the shank 2 is formed on the slider 84. A pin 91 attached on the free end of the grip part 78 engages into this slot 88. In this manner, the grip part 78 is coupled in movement via the slider 84 to the actuation rod 70, for moving the needle 32.

Figures 4, 5:
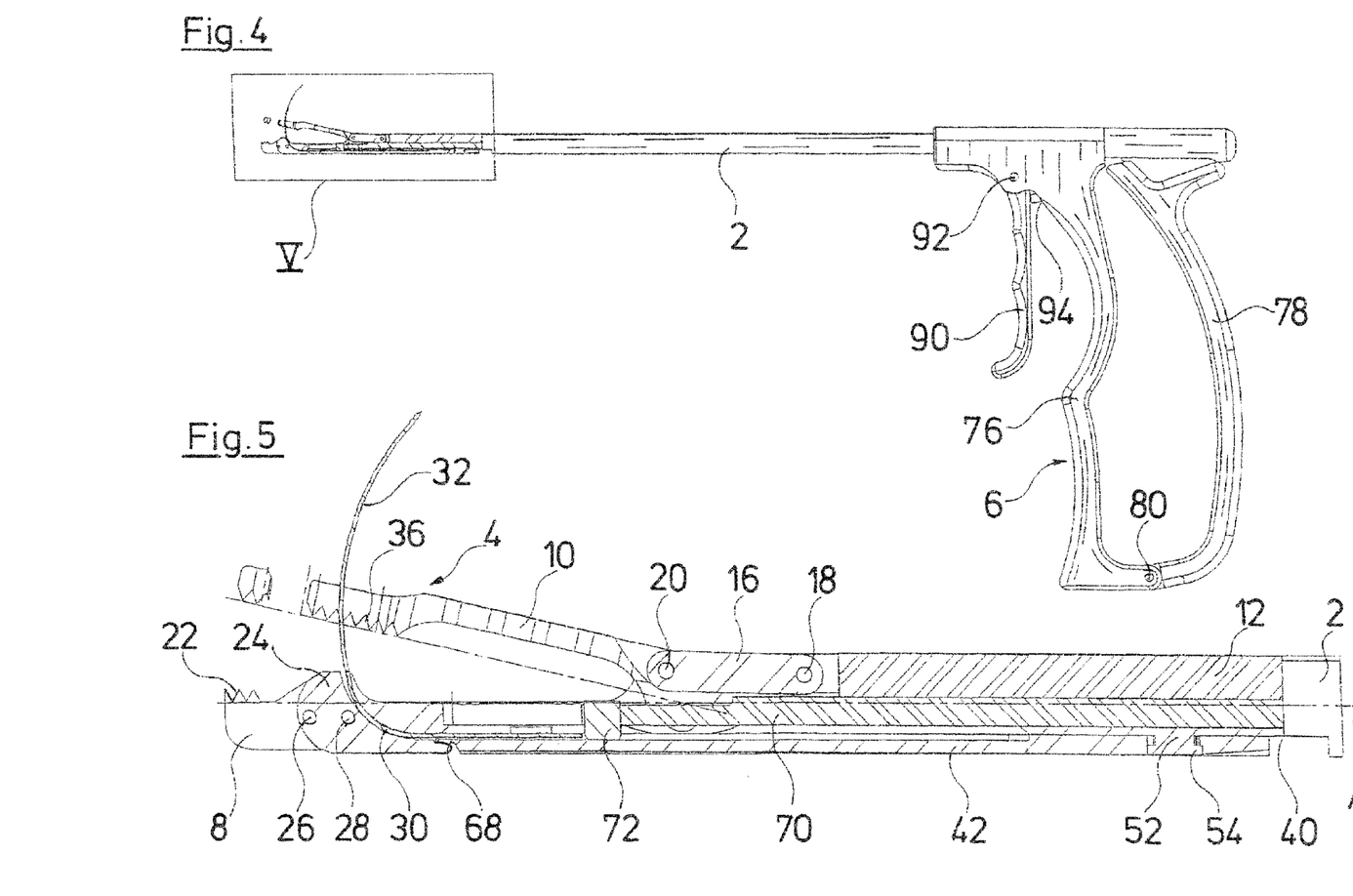
FIG. 4 is a schematic longitudinal view of the surgical suture instrument of FIG. 1, with a moved-out needle.
FIG. 5 is a schematic detail view of portion IV of FIG. 4.

By way of the grip part 78 being pivoted in the direction of the grip part 76, the actuation rod 70 and thus a needle 32 arranged in the needle holder 42 is displaced in the distal direction against the spring force of the helical spring 86. By way of this, as is represented in FIG. 5, the needle 32 goes through the guide channel 30 arranged on the needle guide component 24 and subsequently through the opening 34 formed on the jaw part 10. By way of simply letting go of the grip part 78, the needle 32 with the actuation rod 70 is moved back again into the needle holder 42 by way of the relaxation of the helical spring 86.

An actuation lever 90, distally to the grip part 76, is articulated on the region of the handle 6 forming the extension of the shank 2 via a pin 92. The actuation lever 90 is supported at its side facing the grip part 76 on a pin 94 which is mounted on a helical spring 96 arranged in the grip part 76. A catch 98 is formed on the end of the actuation lever 90 which is arranged in the handle 6, and this catch is in engagement with a recess arranged at the proximal end of the actuation rod 12. If the actuation lever 90 is pivoted against the spring force of the helical spring 96 in the direction of the grip part 76, then the actuation rod 12 is displaced in the distal direction and the jaw part 10 of the forceps jaw 4 is pivoted into an open position by way of this. The actuation rod 12 amid relaxation of the helical spring 96, is displaced proximally again by way of letting go of the actuation lever 90, and the forceps jaw 4 is closed.

Figure 9:
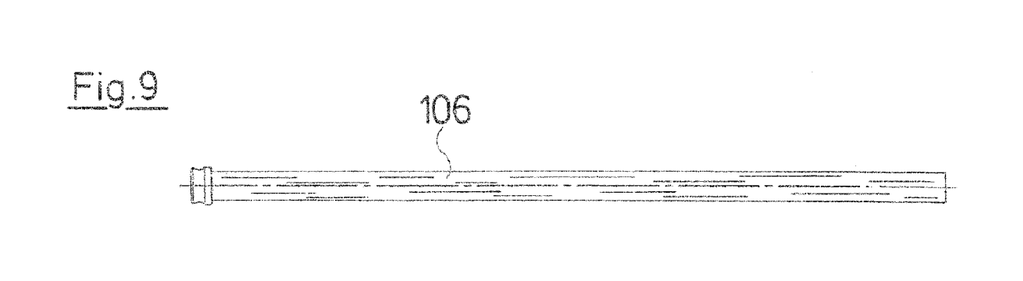
FIG. 9 is a schematic longitudinal view of an outer shank for the surgical instrument of FIG. 1.
Figure 10:
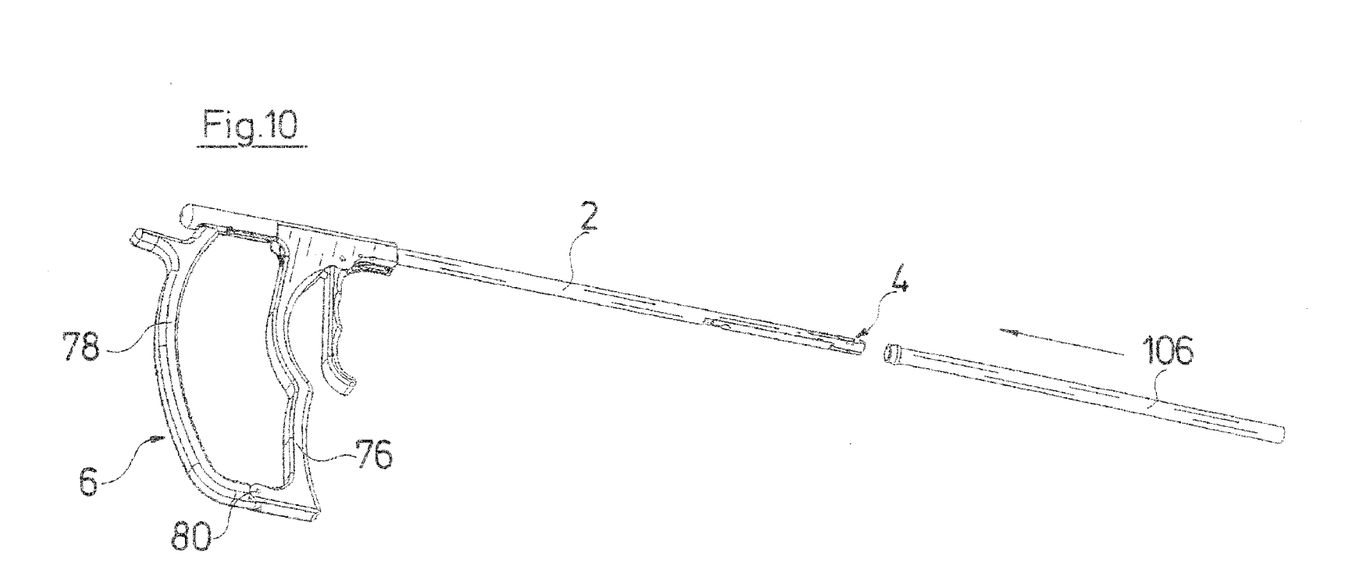
FIG. 10 is a schematic perspective exploded view of the instrument of FIG. 1 with the outer shank of FIG. 9.

On the distal side of the actuation lever 90, a spring 100 is arranged on the region of the handle 6 forming the extension of the shank 2, and this spring is fastened with a screw 102. On the distal side of the spring 100, a ball 104 which forms a locking body of a ball locking connection, connects to this spring. An outer shank 106 which is represented in the FIGS. 9 and 10 and which surrounds the shank 2 in the assembled condition of the surgical suture instrument, may be fixed on the handle 6 by way of this ball locking connection. For this, the outer shank 106 at its proximal end comprises an annular groove 108 into which the ball 104 may engage.

The procedural manner with the surgical suture instrument according to the invention is hereinafter explained by way of FIGS. 11 to 14.

Figure 11:
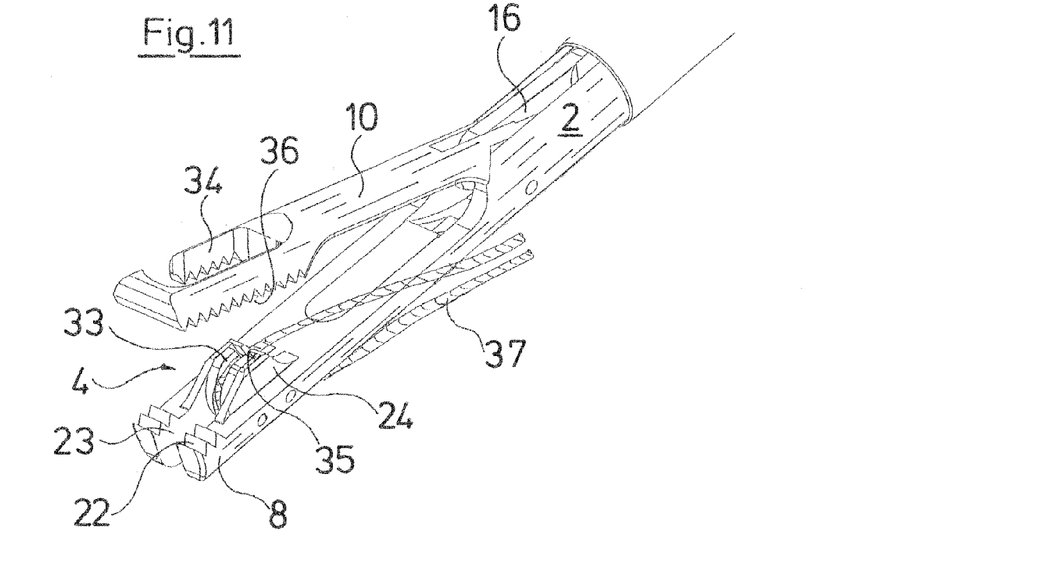
FIG. 11 is a schematic perspective longitudinal view of the distal end region of the instrument of FIG. 1, in a first working position.
Figure 12:
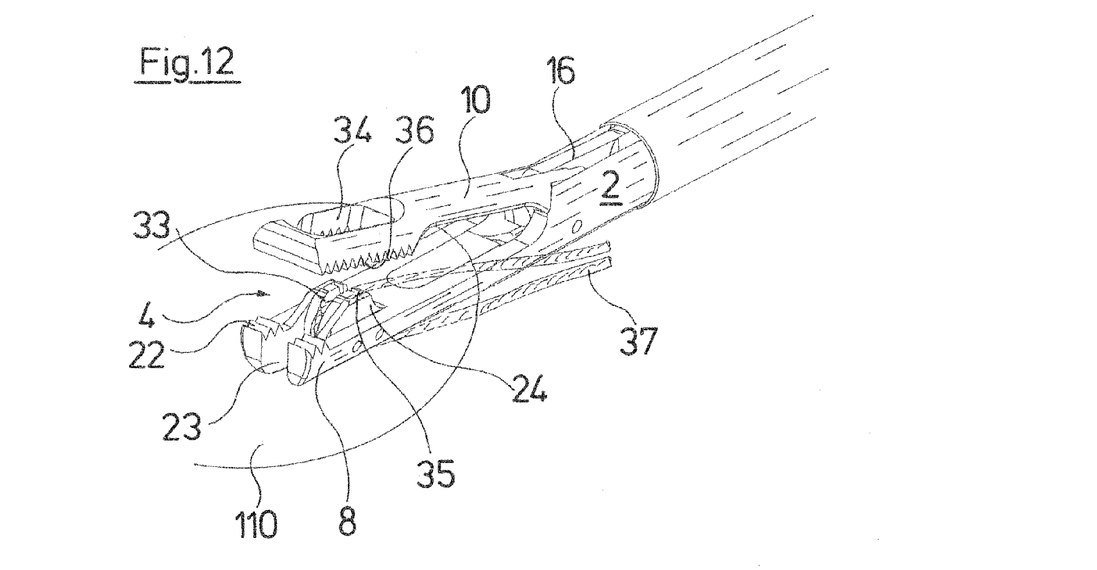
FIG. 12 is a schematic perspective longitudinal view of the distal end region of the instrument of FIG. 1, in a second working position.

Given an opened forceps jaw 4, a thread 37 is applied in the manner of a loop into the groove 33 of the needle guide component 24, which forms a thread guide (FIG. 11). The thread 37 now lies directly above the exit portion 35 of the guide channel 30 running through the needle guide component 24. The needle 32 at this point in time is still located in the needle holder 42 (FIG. 5, 6). Subsequently, the tissue 110 to be sutured is gripped with the forceps jaw 4 of the surgical suture instrument (FIG. 12).

Figure 13:
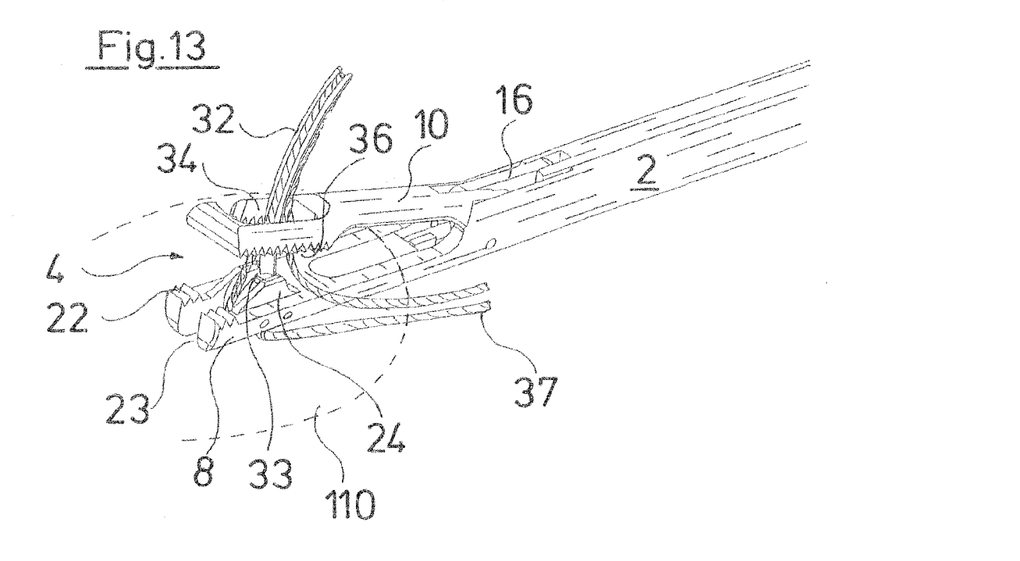
FIG. 13 is a schematic perspective longitudinal view of the distal end region of the instrument of FIG. 1, in a third working position.
Figure 14:
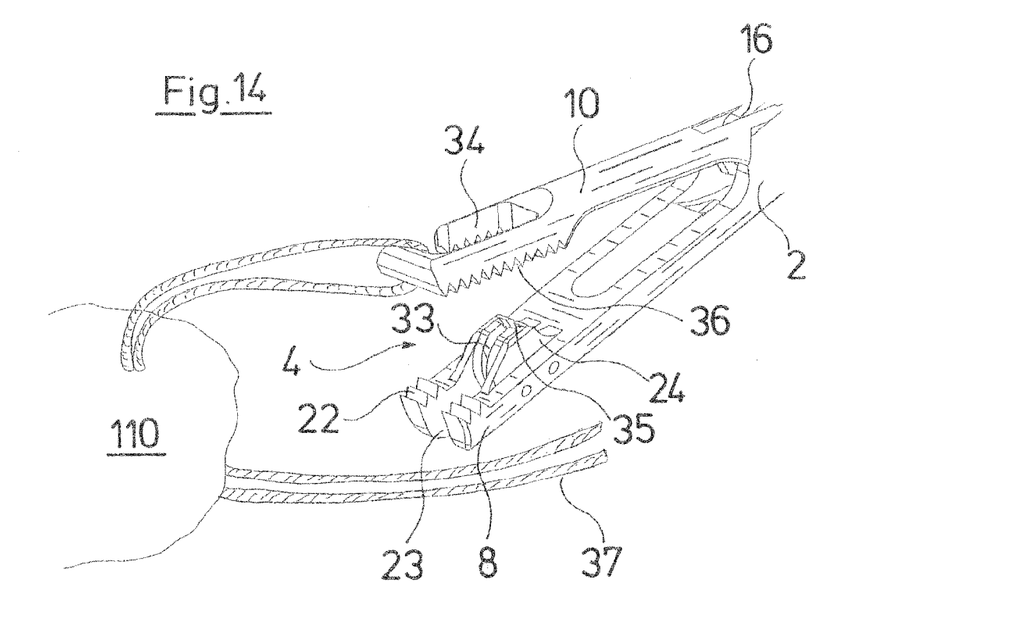
FIG. 14 is a schematic perspective front view of the distal end region of the instrument of FIG. 1, in a fourth working position.

Thereupon, the needle 32 is displaced in the distal direction, wherein the thread 37, when exiting the needle 32 from the run-out of the guide channel 30, is taken from the needle 32. With this, the thread comes to bear in the second region on the groove 68 formed cutting edge of the needle, which is not designed in a cutting manner. Together with the needle 32, the thread 37 is then guided through the tissue 110 (FIG. 13). Subsequently, the needle 32 without the thread 37, is displaced by the springs 86, 120 in the proximal direction back into the needle holder 42. The gripping position of the forceps jaw 4 is released and the loop formed by the thread 37 guided through the tissue is increased in size with the help of the pivotable jaw part 10 (FIG. 14).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A surgical suture instrument comprising: a shank (2) comprising a distal end and a proximal end, a forceps jaw (4) formed on the distal end of the shank and comprising a needle guide (30) formed therethrough, and a receiver (40) formed on the shank (2) for releasable fastening of a needle holder (42), wherein the receiver (40) is connected to the needle guide (30), the needle guide (30) having a distal end and a proximal end, and the receiver (40) being connected to the needle guide (30) on the proximal end of the needle guide (30), the needle holder (42) which comprises a holder needle guide (44) for receiving and guiding a needle (32), wherein the needle holder (42) is configured to be releasable fastened on the receiver (40) of the shank (2) such that the holder needle guide (44) in the needle holder (42) is connected with the needle guide (30).

2. The surgical suture instrument according to claim 1, further comprising fasteners for the releasable fastening of the needle holder (42) on the receiver (40) on the shank (2), the fasteners being provided on the shank (2) and/or on the needle holder (42).

3. The surgical suture instrument according to claim 1, wherein a projection (52) extending transversely to a longitudinal direction of the shank (2) is arranged on the shank (2), and an end region (54) of the projection is widened in at least one direction transversely to the longitudinal direction of the projection (52).

4. The surgical suture instrument according to claim 1, wherein a thread guide (33) is formed on a jaw part (8) of the forceps jaw (4), and the thread guide crosses the needle guide (30).

5. The surgical suture instrument according to claim 1, further comprising an actuation rod (70), wherein the actuation rod comprises an engagement device (72) for engagement with a needle (32) inserted in the needle holder (42), and the engagement device is in a region of the receiver (40) which corresponds to the needle holder (42).

6. The surgical suture instrument according to claim 1, wherein the needle holder (42) is removable from the receiver (40) in a direction perpendicular to a longitudinal axis of the needle holder (42).

7. The surgical suture instrument according to claim 1, further comprising a projection (52) in the receiver (40), at least a portion of the projection extending radially outwardly away from the shank (2), the projection (52) corresponding to a hole (48) in the needle holder (42), wherein the needle holder (42) is attached to the shank (2) by inserting at least a portion of the projection (52) into the hole (48).

8. A surgical suture instrument comprising:
 a shank (2) having a distal end and a proximal end;
 a forceps jaw (4) formed on the distal end of the shank;
 a guide channel (30) extending through at least a portion of the forceps jaw;
 a recess (40) formed in an exterior surface of the shank (2); and
 a needle holder (42) including a groove (44) sized and shaped to receive and guide a needle (32) therein, the needle holder being releasably engageable within the recess of the shank, the groove being aligned with the guide channel when the needle holder is positioned in the recess so that the needle is displaceable from the groove directly into the guide channel.

9. The surgical suture instrument according to claim 8, wherein the needle holder (42) is removable from the recess (40) in a direction perpendicular to a longitudinal axis of the needle holder (42).

10. The surgical suture instrument according to claim 8, further comprising:
 a projection (52) in the recess (40), at least a portion of the projection extending radially outwardly away from the shank; and
 a hole (48) formed in the needle holder (42),
 wherein the needle holder (42) is attached to the shank (2) within the recess (40) by inserting at least a portion of the projection (52) into the hole (48).

* * * * *